United States Patent [19]

Goldstein

[11] Patent Number: 5,752,510
[45] Date of Patent: May 19, 1998

[54] NASAL AND ORAL AIR PASSAGEWAY DELIVERY MANAGEMENT APPARATUS

[76] Inventor: Joseph Goldstein, 1515 Palisades Dr., Suite M, Pacific Palisades, Calif. 90272

[21] Appl. No.: 749,228

[22] Filed: Nov. 14, 1996

[51] Int. Cl.⁶ .................... A61M 15/08; A61M 16/00; A62B 7/00; A62B 9/06
[52] U.S. Cl. .................. 128/207.18; 128/200.24; 128/204.18; 128/207.14
[58] Field of Search .................. 128/200.29, 204.18, 128/207.14, 207.18, 859, 860, 861, 862, 202.28, 205.25, 206.21, 848

[56] References Cited

U.S. PATENT DOCUMENTS

| | | | |
|---|---|---|---|
| 780,709 | 1/1905 | Craig | 128/207.18 X |
| 804,272 | 11/1905 | Schwarz | 128/207.18 X |
| 3,508,543 | 4/1970 | Aulicono | 128/207.18 X |
| 3,730,179 | 5/1973 | Williams | 128/204.18 |
| 4,592,351 | 6/1986 | Smith et al. | 128/207.17 |
| 5,273,032 | 12/1993 | Borody | 128/207.14 |
| 5,375,593 | 12/1994 | Press | 128/207.18 |
| 5,537,994 | 7/1996 | Thornton | 128/204.18 |
| 5,645,046 | 7/1997 | Kay | 128/201.18 |

Primary Examiner—Aaron J. Lewis
Assistant Examiner—Dinh X. Nguyen
Attorney, Agent, or Firm—Allan M. Shapiro

[57] ABSTRACT

Apparatus for alleviating a variety of breathing disorders, having a moldable mouthpiece clamped between the upper and lower teeth of the user so that a bracket outwardly projects from between the lips of the user in cantilevered fashion. The mouthpiece maintains the lower jaw forward to alleviate snoring problems by maintaining the throat clear. A nasal air delivery device is supported on the bracket and includes a pair of breathable air conducting tubes which terminate immediately adjacent to the user's nostrils. A sealing device disposed between the bracket and the nose prevents breathable air leakage, and a chin support carried on the tubes cooperates with the mouthpiece to stabilize and retain the nasal air delivery device in position on the facial area of the user.

15 Claims, 2 Drawing Sheets

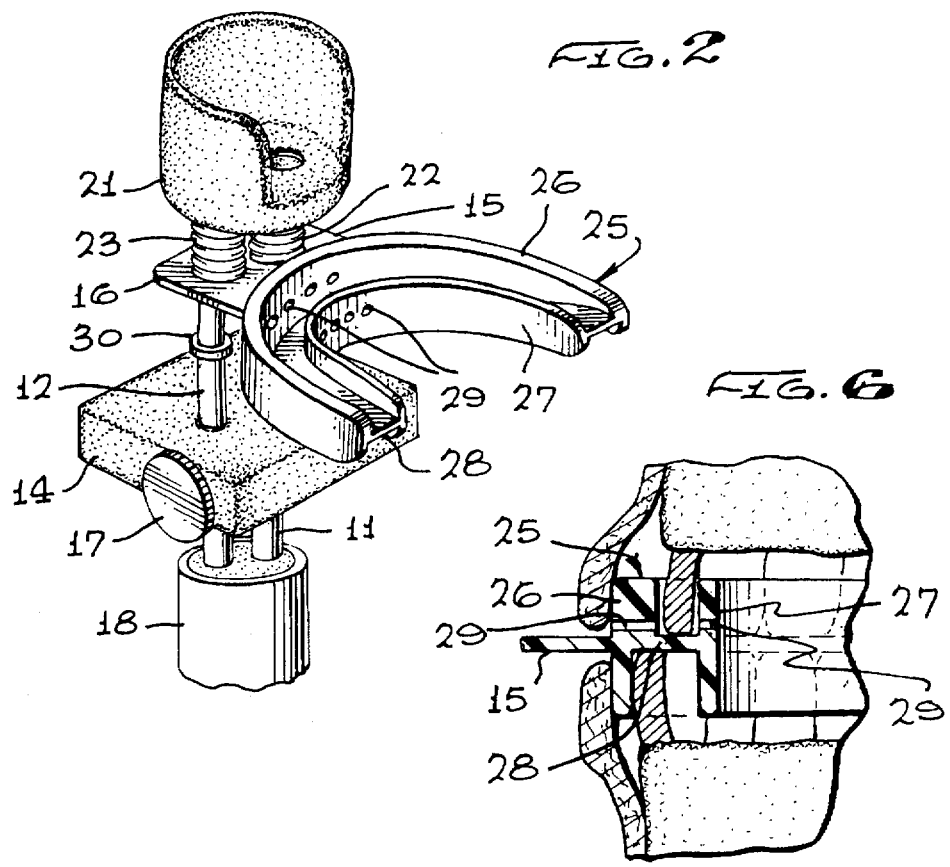
FIG. 2
FIG. 6
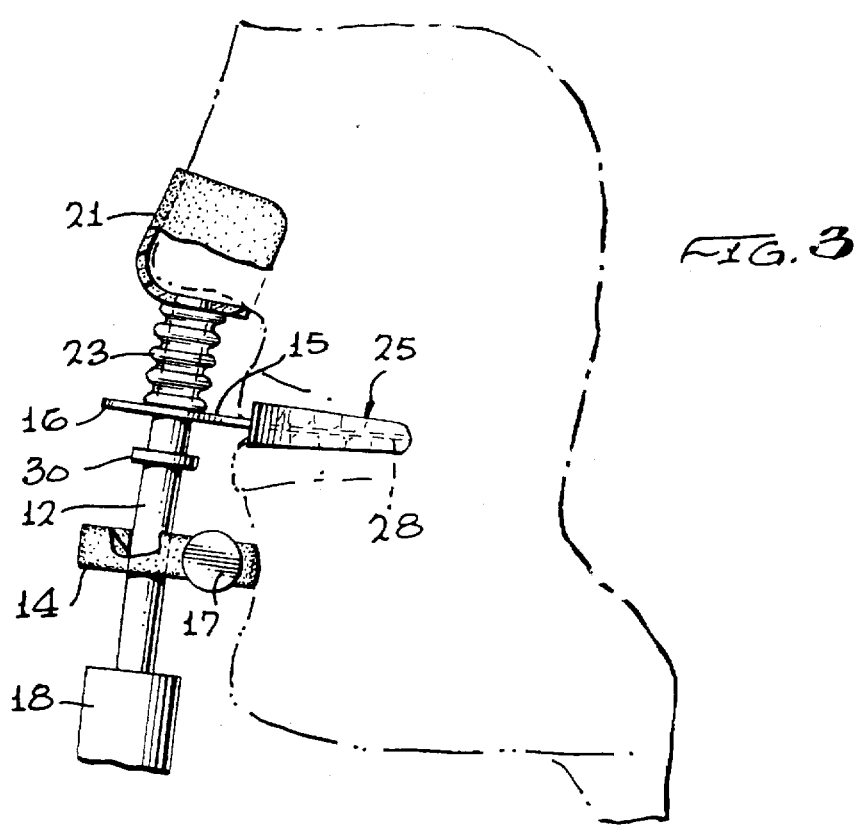
FIG. 3

NASAL AND ORAL AIR PASSAGEWAY DELIVERY MANAGEMENT APPARATUS

BACKGROUND OF THE INVENTION

1. Field of the Invention

The present invention relates to breathing apparatus, and more particularly to a novel air administering and delivery means for introducing breathable air to a patient via nasal and oral passageways during a sleeping procedure so as to avoid a variety of breathing disorders.

2. Brief Description of the Prior Act

In the past, a variety of obstructive sleep disorders or conditions have been encountered by persons, such as sleep apnea, snoring or the like. These are generally conditions in which the person's airways, either nasal or oral, become blocked or restricted during sleep which, in turn, cuts off the brain's supply of oxygen or impairs the flow of oxygen to the person's lungs. Prior attempts have been made to provide apparatus for alleviating a patient's suffering from such breathing disorders which generally are limited to devices for adjusting a user's breathing patterns by adjusting the airflow to consistently deliver breathable air to either the nose passageways or to the mouth and throat passageways. By providing breathable air to the nasal passageways, the adverse effects of sleep apnea and other breathing disorders are alleviated.

By employing apparatus for delivering or administering breathable air to the throat passageways of the user, it will sometimes alleviate disorders connected with snoring or the like. Usually snoring occurs due to blockage of throat passageways. Apparatus used to provide breathable air via nasal passageways may alleviate sleep apnea but have no positive effect in connection with prevention of snoring disorders. Such prior apparatus are concerned with either one or the other delivery systems and make no effort to combine or provide means for handling both types of breathing disorders. Furthermore, prior apparatus are unstable and cumbersome to wear and generally are unsupported about the user's face so that the device is not maintained in a fixed position on the head of the user during sleep. This instability renders prior devices useless since nasal or oral insertions fall from the nose or mouth of the user, depriving the user of the benefits from the systems.

Some attempts have been made to stabilize breathing devices on the head of the user employing an arrangement of elastic or specially buckled straps. In other instances, reliance on supporting the breathing device involves placing the device in the nose or mouth of the user which may cause pain, distortion and injury to the user's facial area.

Prior attempts to solve these problems are disclosed in U.S. Pat. Nos. 4,944,310; 5,537,994; 5,474,060 and 5,065,756. Difficulties and problems have been encountered with these prior systems, assemblies and devices which stem from the fact that such apparatus is limited to certain breathing disorders or conditions relating to either nasal or throat air passageways but not to both. Most prior devices do not provide a stabilizing or mounting system for adequately supporting the apparatus about the facial area of the user so that the apparatus will not fall from or be dislodged from the air passageways during sleep. Prior apparatus is concerned with either one or the other delivery system to nose or mouth; however, no effort is made to combine or provide a means for handling both types of breathing disorders. Conventional face masks may cover both nose and mouth for air delivery, but such air delivery is not for alleviation of breathing disorders.

Therefore, a long standing need has existed to provide a novel means for mounting, stabilizing and maintaining breathing apparatus about the facial area of a person suffering from breathing disorders whereby breathable air conducting conduits of the apparatus are maintained in position with respect to nasal passageways and which positions the user's jaw to clear the throat passageway. Such maintenance and stabilizing support means should be without the need for other straps or head attachment devices. Also, such novel means should include the mounting and holding of the breathable air delivery system in the nose while simultaneously maintaining the user's lower jaw forward to clear his throat passageway.

SUMMARY OF THE INVENTION

The above problems and difficulties are avoided by the present invention which provides a stabilizing device for medical appliances that are supported by the clenched teeth of the user incorporating a bracket extending from the mouth for holding an air delivery system in contact with nasal passageways. In one example, a deformable mouthpiece accepts the upper and lower teeth of the user in a double bite with a flat bracket extending outwardly from the mouthpiece through the lips of the user to terminate in a cantilevered end. An air supply means is employed for delivering breathable air to a pair of air conducting tubes supported on the bracket end so that tips of the tubes terminate with a nose cap disposed on the nose of the user. Resilient bellow means are compressed between the bracket end and the underside of the nose cap to gently maintain the tubes in place adjacent the nostrils. The soft, pliable nose cap is carried on the end of the bellow means and is operable therewith to seal the entrance to the nasal passageways. Stabilizing means in the form of a chin cushion carries the tubes in spaced relationship to the underside of the bracket adapted to bear against the chin of the user to cooperate with the bracket to maintain the nose tubes in place. Adjustment means may be provided on the stabilizing means for determining the extended length of the tubes through the chin cushion and the bracket end.

Therefore, it is among the primary objects of the invention to provide a novel means for alleviating respiratory ailments by providing an air delivery system which not only stabilizes and supports nasal tubes but maintains the user's lower jaw in a forward position.

Another object of the present invention resides in providing a combined dental appliance and nasal air delivery system that anchors or stabilizes the system from a mouthpiece and the user's chin.

Another object resides in a nasal air delivery device/system to be worn during sleep which is comfortable and efficient wherein anchoring and stabilizing of the device about the facial area of the user is achieved without the use of straps, headbands or the like.

Yet another object of the invention is to provide a novel device which not only stabilizes and seals a nasal air delivery system to the user's nose but positions the user's jaw forward to maintain the throat clear whereby many respiratory ailments are avoided.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 2 is a rear perspective view of the apparatus shown in FIG. 1;

FIG. 3 is an enlarged transverse cross-sectional view of the apparatus;

FIG. 6 is an enlarged fragmentary view, in section, illustrating the molded bite of the user's teeth into the dental appliance employed in the apparatus of FIGS. 1–3 inclusive.

DESCRIPTION OF A PREFERRED EMBODIMENT

Figure 1:
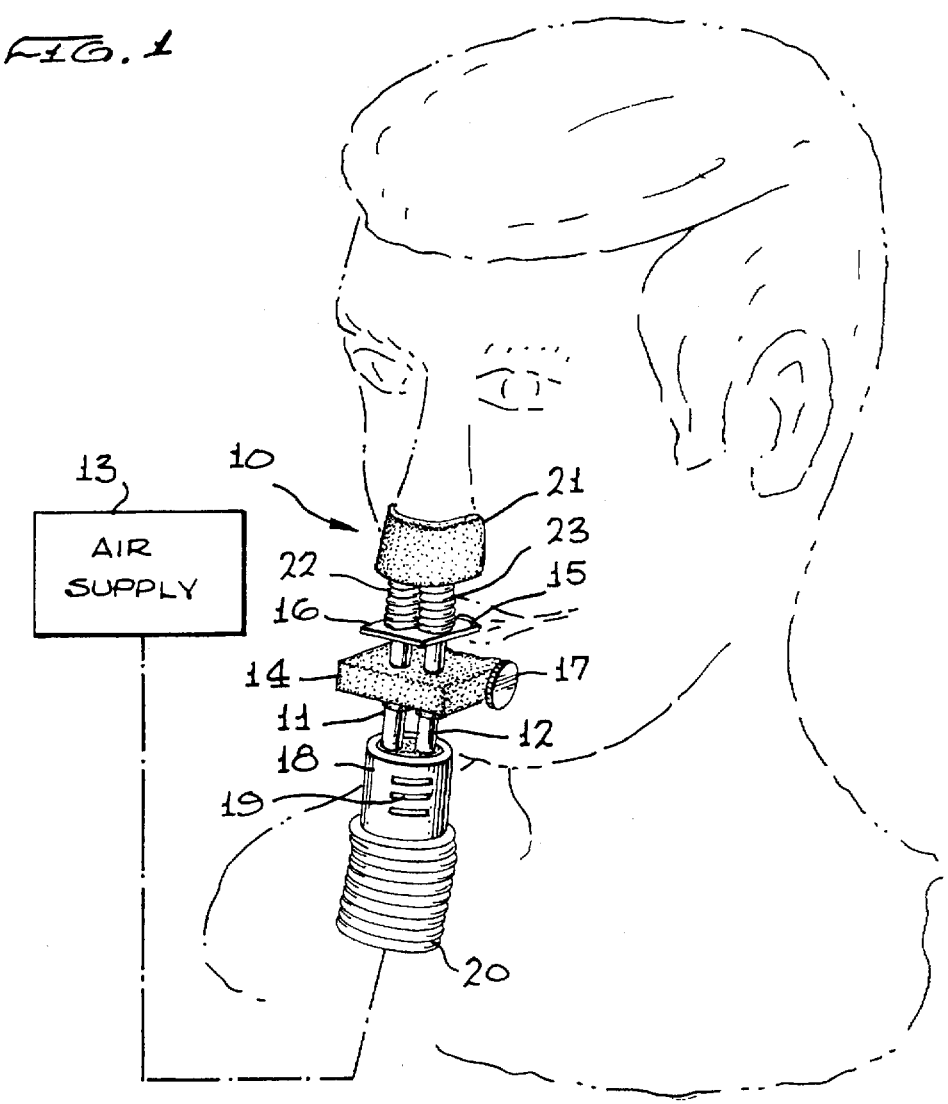
FIG. 1 is a front perspective view of the nasal air delivery and mouth support apparatus of the present invention.

Referring to FIG. 1, the novel nasal air delivery and mouth support is indicated generally by arrow 10 and which includes a pair of elongated tubes 11 and 12 for conducting a supply of breathable air from a conventional air source 13 to the nose passageways of the user. The tubes are adjustably carried on a cushioned support 14 and are supported on a bracket 15 that includes a terminating end 16 cantilevered outwardly from the user's mouth. The opposite end of the support 15 is carried on a dental appliance such as a mouthpiece 25 (illustrated in FIGS. 2 and 5) that is disposed between the teeth of the user providing a double bite. Means for adjusting the angle of the tubes with respect to their support 15 is achieved by rotating an eccentric cam 32 within the cushioned support 14 by means of a finger grasping knob 17. One end of each tube 11 and 12 is disposed within a connector fixture 18 carried on the end of an air supply or delivery hose 20 while the opposite end of each tube is terminated at the nostrils of the user and are sealed with respect to the nose by means of a pliable or soft cup 21. A pair of bellows 22 and 23 are disposed about respective tubes 11 and 12 and are compressed between the cup 21 and the end 16 of the support bracket 15. Therefore, it can be seen that pressurized breathable air is supplied from the source 13 via the hose 20 and connector 18 to the respective tubes 11 and 12. The breathable air continues through the tubes to the nose of the user, while the combination of cup 21 with the bellows 22 and 23 serves as a seal to insure delivery of the breathable air directly to the user's nose without leakage.

Support and anchoring for the apparatus is provided by the support bracket 15 attached to the mouthpiece 25. Adjustment of the knob 17 increases or decreases the distance of the tubes 11 and 12 from the user's chin because the chin support 14 presses against the chin, thus permitting adjustment of the angle of the tubes 11 and 12 in front of the face to accommodate differences in physiognomy, i.e., relative locations of the nose, mouth and chin.

Referring to FIG. 2, it can be seen that the support bracket 15 is secured to the mid-section of an arcuate anchor mouthpiece or dental appliance, indicated generally at 25. The anchor mouthpiece 25 is semi-circular and includes an outer rim 26 with an inner rim 27. The two rims are joined by a section 28 against which the upper and lower teeth of the user are clamped when the apparatus is in position for use. The mouthpiece or anchor 25 preferably is composed of suitable, pliable material which may be softened through the application of heat so that, when introduced into the mouth of the user, the user's teeth can be placed against the section 28 and held in firm and anchoring relationship with respect to the other components of the apparatus.

FIG. 2 also illustrates the communication of the tubes 11 and 12 with the nosepiece 21 so that breathable air is introduced to the nostrils of the user's nose. Also, it can be seen that each of the respective tubes includes a stop member 30 which limits the movement of the tubes between the chin anchor 14 and the end 16 of the bracket 15.

Referring now in detail to FIGS. 3 and 6, it can be seen that the mouthpiece 25 is disposed in the mouth of the user with the user's upper and lower teeth clamped against the section 28 between the inner and outer rims 27 and 26 respectively. The thickness of the section 28 absorbs the clamping load forces applied by the jaw closure whereby the lower jaw is moved and held forward to clear throat internal passageways to the lungs. Likewise, the nostrils of the user are sealed so that the apparatus provides breathable air to the nasal passageways. Therefore, both breathing disorders such as sleep apnea and snoring are greatly alleviated if not eliminated.

Figure 4:
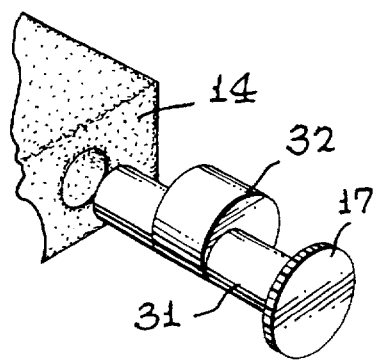
FIG. 4 is an exploded perspective view of an adjustment means employed in the apparatus of FIGS. 1–3 inclusive.
Figure 5:
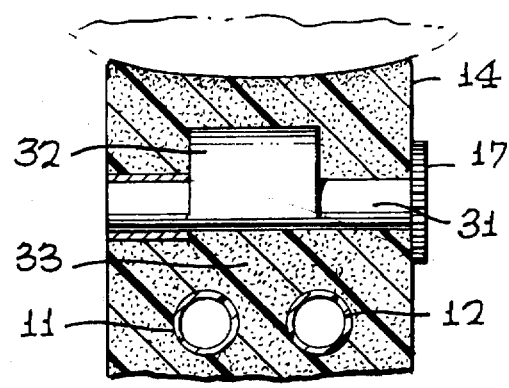
FIG. 5 is a cross-sectional view of the adjustment means shown in FIG. 4.

Referring now in detail to FIGS. 4 and 5, the knob 17 is connected to one end of a turning shaft 31 having an eccentric cam 32 carried on its midsection. As more clearly illustrated in FIG. 5, as the shaft 31 is rotated, the eccentric portion 32 applies more or less pressure against the chin by the interposed material at the midsection of the chin anchor or support 14.

In actual practice, the apparatus of the present invention is introduced to the user by initially heating the pliable or moldable material of the mouthpiece 25 so that, when placed in the mouth of the user, both the upper and lower jaws are compressed whereby the teeth press against the section 28 of the mouthpiece or anchor and in this way a double bite is produced which causes the lower jaw to move forward to clear the user's throat airway. Thus, the adverse affects of a snoring disorder are avoided. The nosepiece 21 is placed over the nose of the user so that the ends of tubes 11 and 12 are immediately adjacent to the nasal passageways of the user. A sealing relationship between the nose is produced by employment of the expanding bellows 22 and 23 which bear against the underside of the nosepiece or cup 21 and the upper side of the support end 16 of support 15. The bellows ends are suitably secured to the underside of the nosepiece by conventional adhesive or the like. It is to be particularly noted that the tubes 11 and 12 are supported by the bracket 15 which is fixedly secured to the outside rim 26 of the mouth appliance or piece 25. Therefore, when the mouthpiece is anchored by means of the user's teeth, the bracket 15 is supported and the cantilevered end 16 holds the tubes 11 and 12 in place. To further augment support, the cushioned chin support 14 places one end against the chin of the user immediately below the lower lip and, since the tubes 11 and 12 are carried by the cushioned support 14, support of the apparatus is improved thereby. It can be seen that the appliance is supported by the mouth and chin of the user and that straps or other elastic bands or the like are unnecessary and that the anchoring means comprising the mouthpiece and chin support are adequate to hold the apparatus in position even during sleep movements. The nasal air supply from source 13 is of a conventional apparatus and, through the use of the present invention, alleviates the adverse affects of sleep disorders such as sleep apnea while the mouthpiece 25 maintains the air passageways of the throat open since the mouthpiece 25 insures that the user's lower jaw would be maintained in a forward position so that the throat airway is clear.

With a near-perfect fit to the nose by the sealing means with the nose and the near-perfect fit of the mouthpiece, all exhalation will be through vents 19 in fitting 18. In the event of a power failure, for example, the only source of air for inhalation would be through the vents 19. The mouthpiece 25 has several holes 29 in the front rim 26 to permit breathing through the user's mouth, if necessary.

While particular embodiments of the present invention have been known and described, it will be obvious to those skilled in the art that changes and modifications may be made without departing from this invention in its broader aspects and, therefore, the aim in the impendent claims is to cover all such changes and modifications as fall within the true spirit and scope of this invention.

What is claimed is:

1. Apparatus for alleviating a variety of breathing disorders comprising:

a mouthpiece adapted to receive upper and lower teeth in a double bite relationship;

a bracket secured to said mouthpiece extending outwardly in a cantilevered relationship from said mouthpiece;

a breathable air delivery device mounted on said bracket whereby applied loads of said breathable air delivery device are transferred to said mouthpiece;

said breathable air delivery device having breathable air conduit means supported on said bracket and terminating immediately adjacent the nostrils of the user;

a pressurized source of breathable air controllably connected to said breathable air conduit means; and stabilizing means carried on said breathable air conduit means adapted to bear against the chin of the user in cooperative relationship with said mouthpiece and said bracket to support said breathable air delivery device; and a sealing means carried on said breathable air conduit means for preventing air leakage between said breathable air conduit means and the user's nose, said sealing means including a cushioned nosepiece secured to said breathable air conduit means and a compressible bellows disposed between said bracket and said nosepiece.

2. Apparatus for alleviating a variety of breathing disorders comprising:

a mouthpiece adapted to receive upper and lower teeth in a double bite relationship:

a bracket secured to said mouthpiece extending outwardly in a cantilevered relationship from said mouthpiece;

a breathable air delivery device mounted on said bracket whereby applied loads of said breathable air delivery device are transferred to said mouthpiece;

said breathable air delivery device having breathable air conduit means supported on said bracket and terminating immediately adjacent the nostrils of the user;

a pressurized source of breathable air controllably connected to said breathable air conduit means; and stabilizing means carried on said breathable air conduit means adapted to bear against the chin of the user in cooperative relationship with said mouthpiece and said bracket to support said breathable air delivery device, adjustment means carried on said stabilizing means for selectively positioning said stabilizing means on said breathable air conduit means.

3. The invention as defined in claim 2 wherein:

said adjustment means includes an eccentric cam having a finger grasping knob for turning said eccentric cam into and out of effective engagement with the user's chin to hold said stabilizing means in a selected position thereon.

4. Airway delivery and management apparatus for the nose and the throat comprising:

a moldable mouthpiece having a support bracket secured thereto and extending outwardly through the lips of the user to terminate in a cantilevered end;

a nasal air delivery device carried on said cantilevered end and having a pair of breathable air conducting tubes in parallel relationship terminating immediately adjacent to the nostrils of the nose;

sealing means operably disposed between said bracket cantilevered end and the nose of the user;

a chin support carried on said tubes in spaced relationship to said bracket cantilevered end and cooperating with said mouthpiece to stabilize and maintain said nasal air delivery device in position on the facial area of the user; and an expandable bellows carried between said bracket and said sealing means urging said sealing means into sealing relationship with the nose of the user.

5. The invention as defined in claim 4 wherein:

said sealing means is a cushioned nosepiece attached to said tubes.

6. The invention as defined in claim 5 wherein:

said bracket cantilevered end includes a pair of openings occupied by said tubes in each of said openings respectively whereby said tubes are normal and said bracket end is maintained in this relationship by the anchoring support of said mouthpiece and said chin support.

7. The invention as defined in claim 6 wherein:

said mouthpiece is composed of a pliable material subject to initial deformation by heat to accept the upper and lower teeth of the user whereby curing of said pliable material releasably fixes the teeth to said mouthpiece.

8. The invention as defined in claim 7 wherein:

said mouthpiece includes a semi-circular construction having an outer rim and an inner rim separated by and joined by a midsection adapted to receive the user's teeth in a double clamping relationship.

9. The invention as defined in claim 8 including:

a plurality of holes in said outer rim to permit breathing through the user's mouth.

10. Airway delivery and management apparatus for the nose and the throat comprising:

a moldable anchor mouthpiece having a support bracket secured thereto and extending outwardly through the lips of the user to terminate in a cantilevered end;

a nasal air delivery device carried on said cantilevered end and having breathable air conduit means terminating immediately adjacent to the nostrils;

sealing means operably disposed between said cantilevered end of said support bracket and the nose of the user;

support means carried on said breathable air conduit means in spaced relationship to said bracket cantilevered end, abuttingly engaged against the chin of the user, and cooperating with said mouthpiece to stabilize and maintain said nasal air delivery device in position on the facial area of the user; and an expandable means carried between said bracket and said sealing means urging said sealing means into sealing relationship with the nose of the user.

11. The invention as defined in claim 10 wherein:

said nasal air delivery device includes at least one tube having opposite ends;

a nosepiece fixed on a selected end of said tube and a source of breathable air connected to the other end of the tube;

said nosepiece providing said sealing means between said tube and the nose of the user.

12. The invention as defined in claim 10 wherein:

said sealing means includes a cushioned nosepiece mounted on said breathable air conduit means and resilient means disposed between said bracket and said nosepiece urging said nosepiece into sealing relationship with the nose of the user.

13. Airway delivery and management apparatus for the nose and the throat comprising:

an anchor mouthpiece having a support bracket secured thereto and extending outwardly through the lips of the user to terminate in a cantilevered end;

a nasal air delivery device carried on said cantilevered end and having breathable air conduit means terminating immediately adjacent to the nostrils;

sealing means operably disposed between said cantilevered end of said support bracket and the nose of the user; and resilient means carried between said bracket and said sealing means urging said sealing means into sealing relationship with the nose of the user.

14. The invention as defined in claim 13 wherein:

said nasal air delivery device includes at least one tube having opposite ends;

a nosepiece fixed on a selected end of said tube and a source of breathable air connected to the other end of the tube;

said nosepiece providing said sealing means between said tube and the nose of the user.

15. Apparatus for alleviating a variety of breathing disorders comprising:

a mouthpiece adapted to receive upper and lower teeth in a double bite relationship;

a bracket secured to said mouthpiece extending outwardly in a cantilevered relationship from said mouthpiece;

a breathable air delivery device mounted on said bracket whereby applied loads of said breathable air delivery device are transferred to said mouthpiece;

said breathable air delivery device having breathable air conduit means supported on said bracket and terminating immediately adjacent the nostrils of the user;

sealing means operably disposed between said bracket and the nose of the user;

resilient means carried between said bracket and said sealing means urging said sealing means into sealing relationship with the nose of the user; and a pressurized source of breathable air controllably connected to said breathable air conduit means.

* * * * *